(12) United States Patent
Kiraly

(10) Patent No.: US 9,282,933 B2
(45) Date of Patent: Mar. 15, 2016

(54) MAGNETIC RESONANCE ELASTOGRAPHY FOR ULTRASOUND IMAGE SIMULATION

(75) Inventor: Atilla Peter Kiraly, Plainsboro, NJ (US)

(73) Assignee: SIEMENS CORPORATION, Iselin, NJ (US)

( * ) Notice: Subject to any disclaimer, the term of this patent is extended or adjusted under 35 U.S.C. 154(b) by 158 days.

(21) Appl. No.: 13/822,372

(22) PCT Filed: Sep. 14, 2011

(86) PCT No.: PCT/US2011/051485
§ 371 (c)(1),
(2), (4) Date: Apr. 15, 2013

(87) PCT Pub. No.: WO2012/037181
PCT Pub. Date: Mar. 22, 2012

(65) Prior Publication Data
US 2013/0218002 A1   Aug. 22, 2013

Related U.S. Application Data

(60) Provisional application No. 61/383,899, filed on Sep. 17, 2010.

(51) Int. Cl.
| | |
|---|---|
| *A61B 5/055* | (2006.01) |
| *A61B 5/00* | (2006.01) |
| *G01R 33/48* | (2006.01) |
| *A61B 8/08* | (2006.01) |
| *A61B 8/00* | (2006.01) |

(52) U.S. Cl.
CPC ............. *A61B 5/7278* (2013.01); *A61B 5/0035* (2013.01); *A61B 5/0051* (2013.01); *A61B 5/055* (2013.01); *A61B 8/485* (2013.01); *A61B 8/5261* (2013.01); *G01R 33/4814* (2013.01); *A61B 8/4245* (2013.01); *A61B 8/483* (2013.01)

(58) Field of Classification Search
CPC .... A61B 5/0035; A61B 5/0051; A61B 5/055; A61B 5/7278; A61B 8/4245; A61B 8/483; A61B 8/485; A61B 8/5261; G01R 33/4814
See application file for complete search history.

(56) References Cited

U.S. PATENT DOCUMENTS

| | | | | |
|---|---|---|---|---|
| 2003/0233039 | A1* | 12/2003 | Shao et al. | 600/407 |
| 2009/0046912 | A1* | 2/2009 | Hostettler et al. | 382/131 |
| 2010/0049029 | A1* | 2/2010 | Li et al. | 600/410 |

OTHER PUBLICATIONS

Simulating Dynamic Ultrasound Using MR-Derived Motion Models to Assess Respiratory Synchronisation for Image-Guided Liver Interventions; Rijkhorst, et al. In Information Processing in Computer-Assisted Interventions, Springer Berlin Heidelberg, Jun. 23, 2010 (pp. 113-123).

(Continued)

*Primary Examiner* — Ruth S Smith

(57) ABSTRACT

Ultrasound data is simulated using magnetic resonance (MR) elastography. MR elastography provides tissue characteristic information, such as elastic modulus, velocity, or stiffness. This tissue characteristic information indicates a density or viscosity of the tissue, allowing simulation of ultrasound data with MR acquired data. The same MR imaging system may be used to acquire the MR elastography and pre-operative anatomy information. The actual ultrasound information may be registered with simulated ultrasound information for registration of the actual ultrasound information with the MR anatomy information.

16 Claims, 1 Drawing Sheet

(56) References Cited

OTHER PUBLICATIONS

Image-To-Physical Registration for Image-Guided Interventions Using 3-D Ultrasound and an Ultrasound Imaging Model; King, et al. In Information Processing in Medical Imaging, Springer Berlin Heidelberg, Jul. 5, 2009 (pp. 188-201).

Automatic Non-Linear MRI-Ultrasound Registration for the Correction of Intra-Operative Brain Deformations; Arbel, et al. MICCAI 2001. LNCS, vol. 2208, 2001 (pp. 913-922).
Automatic CT-Ultrasound Registration for Diagnostic Imaging and Image-Guided Intervention; Wein, et al. In Medical Image Analysis, vol. 12, No. 5, Oct. 1, 2008 (pp. 577-585).

\* cited by examiner

MAGNETIC RESONANCE ELASTOGRAPHY FOR ULTRASOUND IMAGE SIMULATION

RELATED APPLICATIONS

The present patent document claims the benefit of the filing date under 35 U.S.C. §119(e) of Provisional U.S. Patent Application Ser. No. 61/383,899, filed Sep. 17, 2010, which is hereby incorporated by reference.

BACKGROUND

The present embodiments relate to ultrasound image simulation. Ultrasound images are easily acquired during an interventional or radiotherapy procedure. However, ultrasound images may lack the resolution or detail of computed tomography (CT) images. A CT volume may be acquired prior to the procedure and may be valuable for guidance during the procedure.

By registering the ultrasound images with the pre-operative CT volume, real-time and detailed information are both provided during the procedure. To register these different modalities, the CT volume may be used to simulate an ultrasound image. The pseudo-ultrasound simulations may better register with the actual ultrasound images. To simulate ultrasound from the CT volume, the acoustic properties (e.g., density of tissue) from the CT volume are used. The Houndsfield Unit (HU) from CT may be used as an estimate of density.

Magnetic resonance (MR) imaging may have different or greater variety of functional and/or anatomical information than CT imaging. However, MR imaging does not produce information as closely resembling density as provided by CT imaging. Physical sensors or feature recognition may be used for registration of ultrasound with MR, but sensors and feature recognition may make examination more expensive or difficult or be inaccurate.

BRIEF SUMMARY

By way of introduction, the preferred embodiments described below include methods, systems, instructions, and computer readable media for ultrasound data simulation using magnetic resonance (MR) elastography. MR elastography provides tissue characteristic information, such as elastic modulus, viscosity or stiffness of tissue. This information indicates a density or viscosity of the tissue, allowing simulation of ultrasound data with MR acquired data.

The same MR imaging system may be used to acquire the MR elastography and pre-operative anatomy information, providing both on a same coordinate system. The actual or real-time ultrasound information may be registered with simulated ultrasound information, allowing registration of the actual ultrasound information with the MR anatomy information.

In a first aspect, a method is provided for ultrasound data simulation using magnetic resonance elastography. A magnetic resonance (MR) imaging system is used to obtain MR anatomy data representing anatomy of a patient and MR elastography data representing an elastic characteristic of the anatomy of the patient. Information related to density is derived from the MR elastography data. Model ultrasound data is simulated from the information related to density. Actual ultrasound data is registered with the MR anatomy data as a function of the model ultrasound data.

In a second aspect, a non-transitory computer readable storage medium has stored therein data representing instructions executable by a programmed processor for ultrasound data simulation using magnetic resonance elastography. The storage medium includes instructions for acquiring magnetic resonance (MR) data representing reaction of tissues to propagation of a mechanical wave through the tissues of a patient, and simulating ultrasound data from the tissues of the patient based on the MR data representing the propagation of the mechanical wave through the tissues of the patient.

In a third aspect, a system is provided for ultrasound data simulation using magnetic resonance elastography. A magnetic resonance (MR) system is configured to provide first MR data of an elastic characteristic of tissue of a patient and second MR data of the tissue. A processor is configured to estimate density of the tissue from the MR data and to register the first MR data with the second MR data.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

MR elastography is used to obtain images describing the elastic properties or density of the volume. For registration and/or fusion, ultrasound images are simulated from the elastic properties or density information. Since elastography directly models the material properties of sound waves within the volume, ultrasound images may be accurately simulated through the volume.

A real-time system capable of MR to ultrasound image registration is provided. Such a system may be particularly useful as compared to CT due to less radiation exposure. For example, CT imaging may not be used for breasts due to radiation exposure. Simulation of ultrasound from MR elastography may allow for fusion of real-time ultrasound information with more detailed pre-operative MR anatomy information in procedures for the breast, liver, kidney, or other organs. The ultrasound simulation with MR elastography may be used for registration for diagnosis or treatment of any organ.

Figure 1:
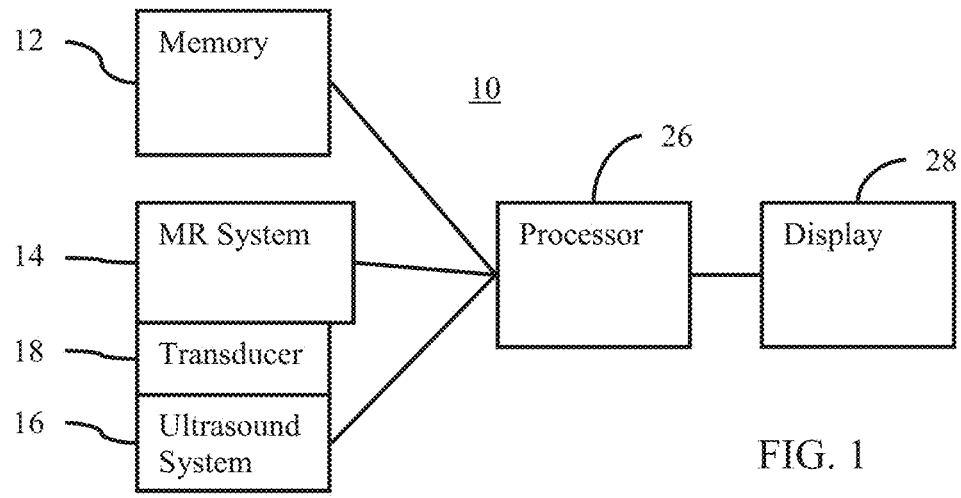
FIG. 1 is a block diagram of one embodiment of a system for ultrasound data simulation using magnetic resonance elastography.

FIG. 1 shows a system 10 for ultrasound data simulation using magnetic resonance elastography. The system 10 includes a memory 12, an MR system 14, an ultrasound system 16, a transducer 18, a processor 26, and a display 28. Additional, different, or fewer components may be provided. For example, a network or network connection is provided, such as for networking with a medical imaging network or data archival system. As another example, separate transducers 18 are used for acquiring MR elastography data and ultrasound data. In another example, a user interface is provided. In yet another example, the ultrasound system 16 and transducer 18 are not provided where the system 10 just generates an ultrasound simulation. The MR system 14 may not be provided in some embodiments, such as where the MR data is acquired by transfer or from storage.

The processor 26 and display 28 are part of a medical imaging system, such as the diagnostic or therapy ultrasound system 16, MR system 14, or other system. Alternatively, the processor 26 and display 28 are part of an archival and/or image processing system, such as associated with a medical records database workstation or server. In other embodiments, the processor 26 and display 28 are a personal computer, such as desktop or laptop, a workstation, a server, a network, or combinations thereof.

The display 28 is a monitor, LCD, projector, plasma display, CRT, printer, or other now known or later developed devise for outputting visual information. The display 28 receives images, graphics, or other information from the processor 26, memory 12, MR system 14, or ultrasound system 16. One or more images representing tissues of a patient are displayed. For example, an image rendered from a three-dimensional data set of MR anatomy information is provided adjacent to an image from real-time ultrasound scanning. Preoperative data (e.g., MR anatomy data) with higher resolution and real-time ultrasound data may be combined (e.g., fused) prior to rendering or after rendering to generate a single image on the display 28. Other images may be displayed, such as a rendering from three-dimensional ultrasound data set or a two-dimensional ultrasound scan. Any of the types of data may be combined to form an image or displayed separately at a substantially same time. For example, preoperative and ultrasound images are displayed separately with or without a separate MR elastography image.

The ultrasound system 16 is any now known or later developed ultrasound imaging system. For example, the ultrasound system 16 includes the transducer 18 for converting between acoustic and electrical energies. Transmit and receive beamformers relatively delay and apodize signals for different elements of the transducer 18. B-mode, Doppler, or other detection is performed on the beamformed signals. A scan converter, memory, three-dimensional imaging processor, and/or other components may be provided.

The transducer 18 is a one-, two-, or multi-dimensional array of piezoelectric or capacitive membrane elements. In one embodiment, the transducer 18 is a handheld or machine held transducer for positioning against and outside of the patient. In another embodiment, the transducer 18 is part of a probe for use within the patient, such as a transesophageal probe. For example, the transducer 18 is a one-dimensional array of elements within or on a catheter used for intervention or a different purpose.

The ultrasound data is output in a polar coordinate or scan converted Cartesian coordinate format. Acoustic energy is used to scan a plane and/or volume. For example, a volume is scanned by sequentially scanning a plurality of adjacent planes. Any format or scan technique may be used. The scanned volume may intersect or include all of the patient volume. For example, the breast is scanned with ultrasound along one or more two-dimensional planes.

The magnetic resonance (MR) system 14 includes a cyromagnet, gradient coil, and body coil in an RF cabin, such as a room isolated by a Faraday cage. A tubular or laterally open examination subject bore encloses a field of view. A more open arrangement may be provided. A patient bed (e.g., a patient gurney or table) supports an examination subject, such as a patient with or without one or more local coils. The patient bed may be moved into the examination subject bore in order to generate images of the patient. Received signals may be transmitted by the local coil arrangement to the MR receiver via, for example, coaxial cable or radio link (e.g., via antennas) for localization.

Other parts of the MR system are provided within a same housing, within a same room (e.g., within the radio frequency cabin), within a same facility, or connected remotely. The other parts of the MR system may include local coils, cooling systems, pulse generation systems, image processing systems, and user interface systems. Any now known or later developed MR imaging system may be used. The location of the different components of the MR system is within or outside the RF cabin, such as the image processing, tomography, power generation, and user interface components being outside the RF cabin. Power cables, cooling lines, and communication cables connect the pulse generation, magnet control, and detection systems within the RF cabin with the components outside the RF cabin through a filter plate.

The MR system 14 is configured by software, hardware, or both to acquire data representing a plane or volume in the patient. In order to examine the patient, different magnetic fields are temporally and spatially coordinated with one another for application to the patient. The cyromagnet 12 generates a strong static main magnetic field $B_0$ in the range of, for example, 0.2 Tesla to 3 Tesla or more. The main magnetic field $B_0$ is approximately homogeneous in the field of view.

The nuclear spins of atomic nuclei of the patient are excited via magnetic radio-frequency excitation pulses that are transmitted via a radio-frequency antenna, such as a whole body coil and/or a local coil. Radio-frequency excitation pulses are generated, for example, by a pulse generation unit controlled by a pulse sequence control unit. After being amplified using a radio-frequency amplifier, the radio-frequency excitation pulses are routed to the body coil and/or local coils. The body coil is a single-part or includes multiple coils. The signals are at a given frequency band. For example, the MR frequency for a 3 Tesla system is about 123 MHz+/−500 KHz. Different center frequencies and/or bandwidths may be used.

The gradient coils radiate magnetic gradient fields in the course of a measurement in order to produce selective layer excitation and for spatial encoding of the measurement signal. The gradient coils are controlled by a gradient coil control unit that, like the pulse generation unit, is connected to the pulse sequence control unit.

The signals emitted by the excited nuclear spins are received by the local coil and/or body coil. In some MR tomography procedures, images having a high signal-to-noise ratio (SNR) may be recorded using local coil arrangements (e.g., loops, local coils). The local coil arrangements (e.g., antenna systems) are disposed in the immediate vicinity of the examination subject on (anterior), under (posterior), or in the patient. The received signals are amplified by associated radio-frequency preamplifiers, transmitted in analog or digitized form, and processed further and digitized by the MR receiver.

The recorded measured data is stored in digitized form as complex numeric values in a k-space matrix. A one or multi-dimensional Fourier transform reconstructs the object or patient space from the k-space matrix data.

The MR system 14 may be configured to acquire different types of data. For example, the MR data represents the anatomy of the patient. The MR data represents the response to the magnetic fields and radio-frequency pulses of tissue. Any tissue may be represented, such as soft tissue, bone, or blood.

The MR system 14 may be configured for acquiring specialized functional or anatomic information. For example, T1-weighted, diffusion, or T2-weighted MR data is acquired.

The MR system 14 is configured for acquiring elastography information. Any MR elastography scan may be used. A mechanical wave is induced within the patient. The mechanical wave may be a longitudinal, shear, or other wave. The mechanical wave is induced by a thumper (e.g., contact force applied to the skin of the patient), an acoustic transducer, or other device. For example, the transducer 18 applies acoustic radiation force focused at one or more locations in the patient. In response to phased summation of the acoustic energy from the elements of the transducer 18, the acoustic energy causes a longitudinal and/or shear wave to propagate from the focal region.

The MR system 14 scans the patient during propagation of the mechanical wave. By repeating the scan multiple times, the shift over time in tissue caused by the mechanical wave is observed. In one embodiment, an oscillating, motion sensitizing field gradient is applied synchronously with the acoustic mechanical waves. The cyclic motion of the spins in the presence of these motion-sensitizing gradients causes a measurable phase shift in the received MR signal. The phase shift is proportional to the displacement amplitude and the number of the cyclic motion-sensitizing gradients. Small amplitude synchronous motion may be measured by accumulating phase shifts over multiple cycles of mechanical excitation and the motion-sensitizing gradient waveform. From the measured phase shift in each voxel, the amplitude of displacement of each voxel is estimated in the reconstructed data.

In another embodiment, data acquired at different times is correlated to track the mechanical wave at different locations. Any correlation may be used, such as minimum sum of absolute differences. The displacement providing the maximum correlation from a reference (e.g., MR data from the tissue at rest) at a give time indicates the motion vector of the tissue.

The displacement amplitude may indicate an elastic characteristic of the tissue. The MR elastography data is the displacement amplitude. In other embodiments, the times of the maximum motion is identified for the locations. The time from the generation of the mechanical wave may be used to determine a velocity of the mechanical wave for each location. The MR elastography data is a velocity or parameter derived from the velocity. The mechanical wave travels through different types of tissue at different velocities. Other MR elastography techniques may be used.

In another embodiment, the MR system 14 is not provided. Instead, the MR data is stored in the memory 12 or received from a data transfer.

The memory 12 is a graphics processing memory, a video random access memory, a random access memory, system memory, random access memory, cache memory, hard drive, optical media, magnetic media, flash drive, buffer, database, combinations thereof, or other now known or later developed memory device for storing data or video information. The memory 12 is part of an imaging system, part of a computer associated with the processor 26, part of a database, part of another system, or a standalone device.

The memory 12 stores one or more datasets representing a three-dimensional patient volume or a two-dimensional patient plane. The patient volume or plane is a region of the patient, such as a region within the chest, abdomen, leg, head, arm, or combinations thereof. The patient volume is a region scanned by the MR system 14 and/or the ultrasound system 16.

Any type of data may be stored, such as medical image data (e.g., ultrasound, MR anatomy data, and/or MR elastography data). The data represents the patient prior to or during treatment or other procedure. For example, MR anatomy and elastography data is acquired prior to a procedure, such as just prior to (same day) or during a previous appointment on a different day. This stored data represents tissue, preferably in a high resolution. The MR elastography data may be at a lower resolution than the MR anatomy data.

For volume data, the stored data is interpolated or converted to an evenly spaced three-dimensional grid or is in a scan format. Each datum is associated with a different volume location (voxel) in the patient volume. Each volume location is the same size and shape within the dataset. Volume locations with different sizes, shapes, or numbers along a dimension may be included in a same dataset. The voxel size and/or distribution may be different for different types of MR data, such as MR anatomy and elastography data. The voxel size and/or distribution may be different for different types of MR data, such as MR anatomy and elastography data. The data coordinate system represents the position of the scanning device relative to the patient, so is the same or may be directly transformed between the MR anatomy and elastography data. Alternatively, the MR anatomy and elastography data are acquired using different MR systems 14 or at different times so that direct transform is not available.

The memory 12 stores data for the relationship between the elastic characteristic of the tissue to density, viscosity, or other parameter related to density. For example, a density for each possible velocity is provided in a look-up table stored in the memory 12. The memory 12 may store a default bone density value. Other information may be stored.

The memory 12 or other memory is a non-transitory computer readable storage medium storing data representing instructions executable by the programmed processor 26 for ultrasound data simulation using magnetic resonance elastography. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 26 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for simulating ultrasound data, registering, and/or generating images. The processor 26 is a single device or multiple devices operating in serial, parallel, or separately. The processor 26 may be a main processor of a computer, such as a laptop or desktop computer, or may be a processor for handling tasks in a larger system, such as in an imaging system. The processor 26 is configured by software and/or hardware.

The processor 26 is configured to estimate density or density related characteristic of the tissue from the MR elastography data. The processor 26 calculates the velocity or other data for or from the MR elastography data. Based on the velocity or other tissue characteristic, the density, viscosity, or other tissue characteristic is estimated by calculation of a relationship function or by look-up table. For example, the density is estimated using a relationship of velocity to density in tissue. In other embodiments, the MR elastography data itself is information related to density, so the processor 26 estimates the density by obtaining the MR elastography data.

The processor 26 may perform other actions for simulation or use of the simulation. For example, the processor 26 assigns a specific density for any density associated with bone. Rather than using the relationship for bone, a default value is assigned. As another example, the processor 26 locates edges of tissue in the MR elastography data and defines the density related information for edges. The edges may be located using MR anatomy data. The MR elastography data at the edges is then replaced based on interpolation or other extrapolation from elastography data spaced from the edges. Other edge definition and value assignment for sharpening the edges may be used.

The processor 26 registers the MR elastography data or the related density or viscosity information to the MR anatomy data. In one embodiment, rigid or non-rigid registration between the MR elastography data and the MR anatomy data is performed. To register, similarities between the data are identified. Image processing may identify features. The user may identify features. Identifying three or more features or one or more features with a corresponding orientation represented by both data sets indicates relative positioning.

Registration based on the data without specifically identifying features may be used. In one embodiment, the processor 26 determines similarity using a correlation, such as a minimum sum of absolute differences, cross correlation, local cross-correlation, autocorrelation, or other correlation. For example, a two or three-dimensional set of data is translated and/or rotated into various positions relative to another set of data. The relative position with the minimum sum or highest correlation indicates a match, alignment, or registration location. This registration is performed for different locations using a kernel defining local data to be used.

The set of data for which the local correlations are performed may be sub-set, such as a region of interest or a decimated set, or may be a full set. The set to be matched may be a sub-set or full set, such as correlating a decimated region of interest sub-set of ultrasound data with a full set of preoperative data.

The relative positioning indicates a translation and/or rotation of one set of data relative to another set of data. The coordinates of the different volumes may be aligned or transformed such that spatial locations in each set representing a same tissue have a same or determinable location.

The processor 26 may simulate the ultrasound data. For example, the processor 26 uses the viscosity or density as a function of spatial location to model propagation of acoustic energy. A one, two, or three dimensional simulation of ultrasound data may be created. By mapping acoustic propagation from an array and corresponding beamformation, a resulting scan may be simulated. Other simulations may be used.

The processor 26 may register the simulated ultrasound information with the actual ultrasound information. The coordinates of the simulated ultrasound information have a known relationship or transform to the MR elastography data. The spatial relationship of the MR elastography to the MR anatomy data is determined by registration. By also registering the simulated ultrasound information to the actual ultrasound information, the position of the actual ultrasound scan relative to the pre-operative MR anatomy or other MR data is determined.

Spatially aligned data may be combined, such as by summing, averaging, alpha blending, maximum selection, minimum selection or other process. For example, preoperative MR anatomy data is combined with actual ultrasound data acquired in real time during a procedure. The combined data set is rendered as a three-dimensional representation. The rendering is from both types of information. In an alternative embodiment, a three-dimensional representation is rendered from the preoperative or other tissue responsive data. An ultrasound image is displayed separately adjacent to the preoperative rendering. The relationship of the scan plane or ultrasound view may be overlaid as a graphic on the preoperative rendering or shown separately. In other embodiments, MR anatomy and ultrasound images representing a same view, volume, and/or plane are displayed adjacent to, overlaid with, or combined with each other.

Figure 2:
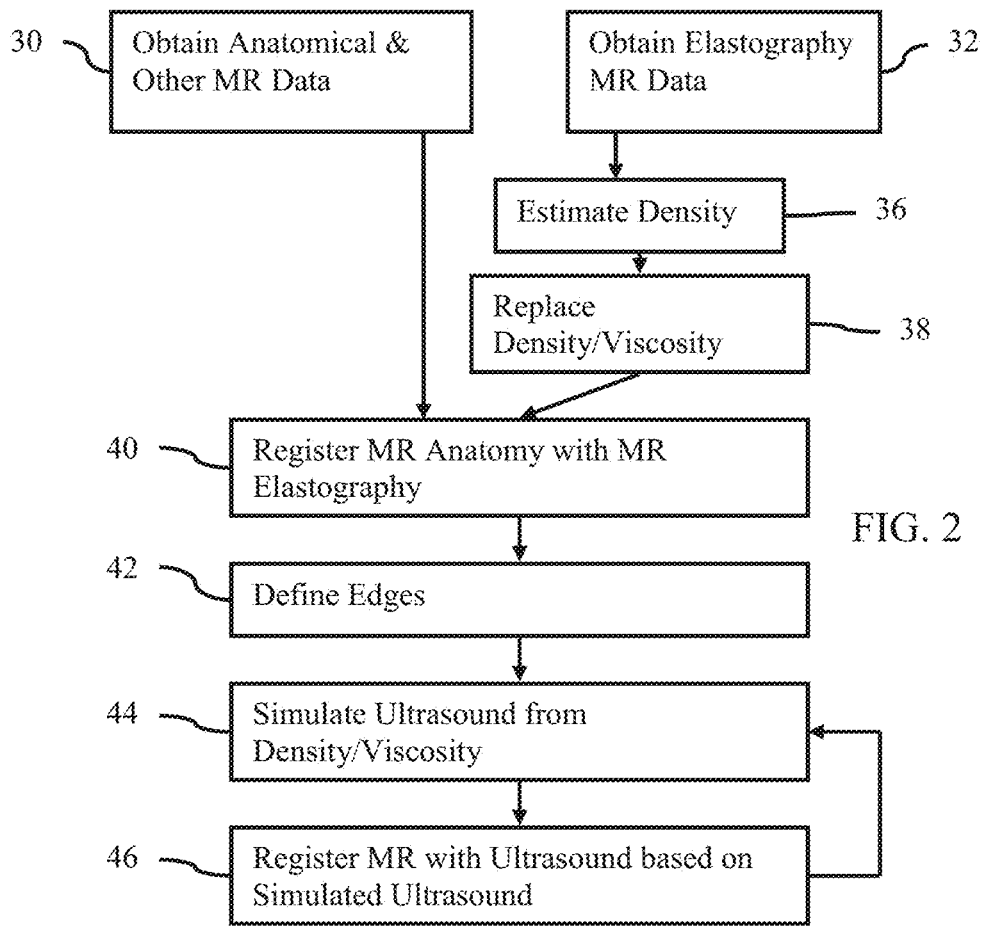
FIG. 2 is a flow chart diagram of one embodiment of a method for ultrasound data simulation using magnetic resonance elastography.

FIG. 2 shows a method for ultrasound data simulation using magnetic resonance elastography. The method is implemented by the system 10 of FIG. 1 or another system. The acts are performed in the order shown or other orders. For example, acts 30 and 32, with or without acts 36, 38, 40, 42, and 44, are performed as part of a pre-operative process the day of or prior to the day of a procedure. Act 46 is performed in real-time with the procedure. Additional, different, or fewer acts may be provided. For example, the replacement act 38 and/or the definition of edges act 42 are not provided. As another example, acts 30, 32, 36, and 44 are provided without other acts. In another example, sensor based registration is also provided.

In act 30, MR anatomy data is obtained. The MR anatomy data is obtained when the patient is scanned or obtained from memory where the patient was previously scanned. The MR anatomy data represents anatomy of a patient. The MR anatomy data serves as a reference for the patient or object being examined.

The MR anatomy data represents a volume of the patient, such as representing voxels in an N×M×O arrangement. Alternatively, the MR anatomy data represents a plurality of separate slices. In other embodiments, the MR anatomy data represents a single plane.

A magnetic resonance (MR) imaging system is used to scan a volume or plane within a patient. One or more transmitters produce an RF excitation field. A desired number of the transmitters are employed and connected through a corresponding number of transmit/receive switches to a corresponding number N of the coils in an RF coil array. The combined RF fields of the coil elements produce a prescribed $B_1$ field throughout the region of interest in the subject.

The signal produced by the subject in response to the RF excitation field is picked up by a coil array and applied to the inputs of the set of receive channels. The received signal is at or around the Larmor frequency. When the $B_1$ field is not being produced, the transmit/receive switches connect each of the receive channels to the respective coil elements. Signals produced by the excited spins in the subject are picked up and separately processed as k-space and/or object space data.

Any MR procedure for acquiring data representing anatomy or tissue may be used. Other MR data may be obtained, such as other anatomical or functional data. For example, T1-weighted or T2-weighted data is obtained. As another example, diffusion data is obtained.

In act 32, MR elastography data is obtained. The MR elastography data is obtained when the patient is scanned or obtained from a previous scan of the patient (i.e., obtained from a memory, such as a PACS system). The MR elastography data represents an elastic characteristic of the anatomy of the patient.

The MR elastography data is distributed in at least two dimensions. For example, the MR elastography data represents a volume of the patient, such as representing voxels in an N×M×O arrangement. The volume arrangement is different than for the MR anatomy data, such as having lesser values for N, M, and O for the same volume. Lower resolution is provided. In other embodiments, the MR elastography data represents a smaller volume (e.g., a region of interest) at lower resolution than the MR anatomy data. Alternatively, the MR elastography data represents a plurality of separate slices. In other embodiments, the MR elastography data represents a single plane. The MR elastography data may be acquired at a same density as the MR anatomy data.

The MR imaging system acquires the data by scanning the patient. Any MR elastography process may be used. In one embodiment, the propagation of a mechanical wave is measured. The mechanical wave is induced in the patient by external pressure, such as cyclical pressure applied to the skin of the patient. For example, a pad is placed on the abdomen of the patient and vibrates as a specific, low frequency. The frequency is low compared to the rate of scanning the region of interest by the MR system. In one embodiment, acoustic energy is used to generate the mechanical wave at a focal region within the patient. The mechanical waves move through stiff and supple tissue at different rates.

To measure the propagation of the mechanical wave, MR scans are performed at different times. The reaction of the tissue to the mechanical wave is measured. The displacement of the tissue caused by the mechanical wave over time, time of travel, and distance indicate a velocity of the mechanical wave through the tissue. A processor determines the stiffness of the tissue based on the characteristic of the displacement. For example, the velocity of the mechanical wave is calculated for each of a plurality of sample locations. The velocity itself is used as the elastography data. Alternatively, peak normalized displacement or a parameter calculated from the velocity and/or peak normalized displacement is used as the MR elastography data. For example, stiffness or strain rate information is used.

In one embodiment, a phase-contrast MR technique using synchronous motion-sensitizing gradients measures the pattern of wave propagation. The resulting data is analyzed to generate quantitative MR elastography data of the stiffness or other mechanical properties of tissue. For example, harmonic low frequency transverse acoustic waves (10 Hz-1.1 kHz) are used as the source of external mechanical stress. The acoustic waves cause tiny cyclic displacements (on the order of tenths of microns). With mechanical waves (e.g., acoustic shear waves), the calculation of regional elastic modulus is simplified, because regional elastic modulus is computed directly from the local wavelength, rather than requiring estimation of the regional static stress distribution. A sensitive MR-based method scans to acquire information about the mechanical waves in tissue. An oscillating, motion sensitizing field gradient is applied synchronously with acoustic mechanical waves that are generated inside the imaged object. The cyclic motion of the spins in the presence of these motion-sensitizing gradients causes a measurable phase shift in the received MR signal. The phase shift is proportional to the displacement amplitude and the number of the cyclic motion-sensitizing gradients. Small amplitude synchronous motion may be measured by accumulating phase shifts over multiple cycles of mechanical excitation and the motion-sensitizing gradient waveform. From the measured phase shift in each voxel, the amplitude of displacement of each voxel is estimated in the reconstructed data. This displacement map shows the mechanical waves propagating within the object. The cyclic motion-sensitizing gradients may be superimposed along any desired axis, and therefore different components of the strain dyadic may be estimated non-invasively. Shear modulus images may be generated using spatial filtering to calculate local wavelength. The local wavelength, displacement, strain, or information derived therefrom is used as the elastography data In act 36, information related to density is derived from the MR elastography data. For example, density or viscosity is estimated from the stiffness or velocity information. The relationship of density or viscosity to velocity, stiffness or other MR elastographic information may be known. Using the MR elastographic information, the density or viscosity is directly estimated. Alternatively, the density or viscosity generally correlates with the elastography information, so a generalized derivation is used. In other embodiments, the stiffness, velocity, or other MR elastographic information is used without further derivation. For example, stiffness is treated as or used as density or viscosity.

The information related to density is derived by calculation. One or more variables, including the MR elastography information, are input to a function for calculating the information related to density. Alternatively, a look-up table or other approach encodes the relationship.

In one embodiment, additional elastography data is obtained in act 32. The mechanical waves are generated at different frequencies at different times. The elastography data is acquired for these different times and thus different frequencies. An average or weighted average is used to combine the elastography data representing the same locations. The information related to density (e.g., density or viscosity) is derived from the average or weighted average.

In act 38, the MR elastography data associated with bone is replaced. The replacement occurs prior to or after the registration of act 40. The data from the elastographic image is used to populate the anatomical image data. Edge sharpening in the anatomical image helps better define boundaries before populating (replacement) with the density information. The replacement may occur prior to or after the derivation of information related to density of act 36. The replacement is of elastography data or derived information related to density.

Bone has a well known density or viscosity. Other tissue may have well known or relatively likely elastic characteristic, density, or viscosity. Bone or other tissue may introduce errors or be less accurately measured for stiffness or elastic characteristic. To avoid errors or artifacts, the information is replaced by the likely or known values.

The tissue (e.g., bone) is identified in the anatomy data. Any segmentation may be used, such as a threshold. For locations associated with the bone or other tissue, the information related to density is replaced. The expected or likely elastic characteristic, density, or viscosity is used. For other locations, the elastography data or derived information related to density is used.

In act 40, the MR elastography data is registered with the MR anatomy data. The MR elastography information may be at a lower resolution than the MR anatomy data. Registering may equalize the resolution and/or locate a tissue of interest (e.g., tumor). The registering provides coordinate information in or a transform to a same system for both the MR anatomy and elastography data.

Due to differences in resolution, some voxels or locations represented by the MR anatomy data may not have corresponding MR elastography data. The registration may up-sample the MR elastography data so that information is provided at each location. All points in the anatomy data have corresponding elastography data. In alternative embodiments, the anatomy data is down sampled or different resolutions are used.

Any registration may be used. The registration is rigid or non-rigid. The elastography data is registered spatially to or with the anatomy data. Since the types of data are different, a local cross-correlation (LCC) cost function may be used for registration. Other registrations may be used, such as minimum sum of absolute differences. To preserve the anatomy information, the anatomy data is used as a reference. The elastography information is non-rigidly warped to the fit the anatomy data. Alternatively, the elastography data is used as the reference.

The registration may result in effective up sampling of the elastography data to the resolution of the anatomy data. For example, registration may tri-linearly interpolate, directly up sample the elastography data.

In act 42, edges represented in the MR elastography or information related to density are defined. Up sampling or registration may result in a lack of detail for edges in the elastographic or density information. The anatomic data may be used to enhance the edge details in the information related to density or elastography data. The edge sharpening is performed before or after the registration of act 40 and/or the estimate of density related information of act 36.

Edges represented in the MR data showing the reaction of tissue to pressure are defined or created at a higher resolution. The definition is a function of the MR data representing the anatomy. The edges are identified from the anatomy information. Using the edge information, the density or viscosity values for edge locations may be determined from adjacent density or viscosity information on a same side of the edge.

In one embodiment, the anatomical data is used to sharpen the edges in the information related to density. A gradient magnitude of the anatomical data is calculated. The connected locations of higher gradient indicate edges. Other boundary detection may be used. The edge locations are indicated separately from other locations, such as using a binary indication. The edge locations are dilated or expanded, such as to include locations within 3 mm or other distance from the edge. The expanded or dilated region is removed from the information related to density, such as the density, viscosity data, or stiffness data. To fill in the removed information, a Random Walker algorithm or other region growing is used. Instead of seeds in the Random Walker defining specific segmentation points, the seeds define densities, viscosities, stiffness values, or other information related to density to be propagated to the edge locations. The interior or clearly tissue related information is expanded to the edges where the edges are determined from the higher resolution anatomy data. Other sharpening may be used.

In act 44, model ultrasound data is simulated. The information related to density is used to create an estimated ultrasound image. The information related to density is used as a basis for the simulated ultrasound data.

Any simulation may be used. For example, the density, viscosity, stiffness, or elastography information is used to estimate the interaction of acoustic energy from a phased array with the tissue. The propagation of acoustic waves and reflections are modeled. The changes in speed of travel due to different density, viscosity, stiffness, or other elastic characteristic are used to model beamformation or ultrasound imaging.

The acoustic interaction is simulated from a plurality of different possible ultrasound transducer locations. The anatomy data may be used to identify or limit the possible transducer locations. A plurality of simulated frames of ultrasound data are generated from the limited number of locations for which a transducer may be placed on and/or within a patient. Correctly estimating the location of the ultrasound probe may help in the registration. Estimating multiple locations may better narrow down the possible images.

In act 46, actual ultrasound data is registered with the simulations. The actual ultrasound data is acquired by acoustically scanning the patient in two or three dimensions. The scan occurs during a procedure, such as during an operation.

The simulation is based on the ultrasound probe being at a particular location. Multiple simulations for different possible probe positions and scan orientations are used. The simulation with the highest correlation or similarity (e.g., minimum sum of absolute differences) to the actual ultrasound data is selected. The selected simulation indicates a position of the actual ultrasound data relative to the MR elastography data. Based on the registration of the MR elastography data with the anatomical data, the actual ultrasound data may be related with the MR anatomy data. By modeling ultrasound data, the actual ultrasound data may be registered with the MR anatomy data.

In one embodiment, the simulated ultrasound data models specific features represented in the information related to density. Gradients or other information associated with the features may be registered to the same features as extracted from the actual ultrasound data.

Registering is performed along two or three-dimensions. Inter-modality 3D-3D registration may provide registration more accurate than 2D-3D or 2D-2D. The registration accounts for rotation along any number of the dimensions. Any combination of translation and rotation degrees of freedom may be used, such as 6 degrees (3 axes of rotation and 3 axes of translation).

The coordinates of the ultrasound and other modality are registered. The data from the ultrasound and MR modality are registered using any now known or later developed data registration. For example, manual alignment of images rendered from the data or automatic image- or data-based registration may be used.

In one embodiment, the data sets prior to rendering are correlated. For example, the ultrasound data is correlated with the data representing the volume. Different translations and rotations between the sets of data are searched and a corresponding similarity value is calculated. The translation and rotation combination with the highest or sufficient correlation indicates the spatial alignment. Any search pattern may be used, such as numerical optimization, course-to-fine searching, subset based searching, or use of decimated data.

The correlation may be based on all of the data in the sets or as a function of at least one feature represented in the ultrasound data and the data representing the volume. For example, the user or a processor identifies features in each data set. The features may be tissue boundaries, tissue regions, bone region, fluid region, air region, combinations thereof, or other feature. The data representing the features with or without surrounding data is used for the correlation. The features may be identified in one set (e.g., ultrasound) for matching with all of the data in another set, or features of one set may be matched to features of another set.

The data may be used for correlation without alteration. In other embodiments, one or both sets of data are filtered or processed to provide more likely matching. For example, higher resolution MR data is low pass filtered, decimated, or image processed to be more similar to ultrasound data.

The registered data may be used to generate one or more images. Separate images for the separate modalities may be provided. The data may be combined using any function to generate one image representing data from the different modalities. Graphical overlays or other information may be presented to the user to indicate relative position. The images are renderings from volume data or are planar representations of a scan plane or a plane through the volume.

Acts 44 and 46 may be repeated as the ultrasound transducer is moved. Given a previous registration, the search for a subsequent registration may be limited or reduced. The size of a search region may be symmetric or asymmetric, such as where the transducer is likely to move along one or two directions and not along a third direction.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for ultrasound data simulation using magnetic resonance elastography, the method comprising:
   obtaining with a magnetic resonance (MR) system MR anatomy data representing anatomy of a patient;
   obtaining MR elastography data representing an elastic characteristic of the anatomy of the patient;
   registering the MR elastography data with the MR anatomy data;
   deriving, with a processor, information related to density from the MR elastography data;
   simulating, with the processor, model ultrasound data from the information related to density;
   acquiring ultrasound data with an ultrasound scanner;
   registering the model ultrasound data with the ultrasound data acquired with the ultrasound scanner;
   registering the ultrasound data acquired with an ultrasound scanner with the MR anatomy data as a function of the model ultrasound data based on the registering of the model ultrasound data with the ultrasound data acquired with the ultrasound scanner; and
   generating an image using the registering of the ultrasound data acquired with the ultrasound scanner with the MR anatomy data.

2. The method of claim 1 wherein obtaining the MR anatomy data comprises obtaining T1-weighted or T2-weighted data.

3. The method of claim 1 wherein obtaining MR elastography data comprises measuring, with the MR system, a propagation of a mechanical wave induced in the patient.

4. The method of claim 1 wherein obtaining the MR elastography data comprises generating an oscillating field gradient in synchronization with acoustic mechanical waves, measuring a phase shift with the MR system, and estimating an amplitude of displacement as a function of the phase shift.

5. The method of claim 1 wherein deriving the information related to density comprises determining density estimates from the MR elastography data.

6. The method of claim 1 wherein deriving the information related to density comprises determining viscosity estimates from the MR elastography data.

7. The method of claim 1 wherein simulating the model ultrasound data comprises simulating acoustic waves through the patient as a function of the information related to density and beamformation of the acoustic waves.

8. The method of claim 1 wherein simulating the model ultrasound data comprises simulating an ultrasound image from the information related to density.

9. The method of claim 1 wherein registering ultrasound data acquired with the ultrasound scanner with the MR anatomy data comprises:
   relating the ultrasound data acquired with the ultrasound scanner with the MR anatomy data based on the registering acts.

10. The method of claim 1 further comprising:
    replacing information related to density representing bone with an expected density or viscosity.

11. The method of claim 1 further comprising:
    defining edges of tissue represented in the MR elastography data as a function of the MR anatomy data.

12. A non-transitory computer readable storage medium having stored therein data representing instructions executable by a programmed processor for ultrasound data simulation using magnetic resonance elastography, the storage medium comprising instructions for:
    acquiring from a magnetic resonance (MR) system MR elastography data representing reaction of tissues to propagation of a mechanical wave through the tissues of a patient;
    deriving density from the MR elastography data representing the propagation of the mechanical wave through the tissues of the patient, the deriving comprising defining edges of the tissues represented in the MR elastography data representing the reaction, the defining of the edges being a function of MR data representing anatomy, the edges being used for deriving the density;
    simulating ultrasound data from the tissues of the patient based on the density derived from the MR elastography data representing the propagation of the mechanical wave through the tissues of the patient; and
    generating an image based on the simulated ultrasound data.

13. The non-transitory computer readable storage medium of claim 12 wherein acquiring MR elastography data representing the reaction comprises acquiring MR elastography data distributed in at least two dimensions.

14. The non-transitory computer readable storage medium of claim 12 further comprising acquiring the MR data representing anatomy, wherein simulating comprises registering the MR elastography data representing the reaction with the MR data representing anatomy, the registering providing MR elastography data representing the reaction at a resolution of the MR data representing the anatomy.

15. A non-transitory computer readable storage medium having stored therein data representing instructions executable by a programmed processor for ultrasound data simulation using magnetic resonance elastography, the storage medium comprising instructions for:
    acquiring from a magnetic resonance (MR) system MR data representing reaction of tissues to propagation of a mechanical wave through the tissues of a patient;
    deriving density from the MR data representing the propagation of the mechanical wave through the tissues of the patient;

simulating ultrasound data from the tissues of the patient based on the density derived from the MR data representing the propagation of the mechanical wave through the tissues of the patient, wherein simulating the ultrasound data comprises replacing MR data associated with bone; and generating an image based on the simulated ultrasound data.

16. A system for registration using magnetic resonance elastography, the system comprising:

a magnetic resonance (MR) system configured to provide first MR data of an elastic characteristic of tissue of a patient and second MR data of the tissue; and a memory storing a relationship of the elastic characteristic of the tissue to density and storing a bone density;

a processor configured to estimate density of the tissue from the first MR data and to register the first MR data with the second MR data based on the estimated density of the tissue, wherein the processor is configured to estimate the density using the relationship, to assign the density associated with bone with the bone density rather than using the relationship, and to define the density for edges of the tissue as a function of the first and second MR data.

* * * * *